United States Patent
Steadman Booker et al.

(10) Patent No.: US 9,753,157 B2
(45) Date of Patent: Sep. 5, 2017

(54) RADIATION DETECTOR WITH HEATING DEVICE

(71) Applicant: KONINKLIJKE PHILIPS N.V., Eindhoven (NL)

(72) Inventors: Roger Steadman Booker, Aachen (DE); Christoph Herrmann, Aachen (DE); Frank Verbakel, Helmond (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/036,561

(22) PCT Filed: Sep. 15, 2015

(86) PCT No.: PCT/EP2015/070992
§ 371 (c)(1),
(2) Date: May 13, 2016

(87) PCT Pub. No.: WO2016/046014
PCT Pub. Date: Mar. 31, 2016

(65) Prior Publication Data
US 2017/0192110 A1    Jul. 6, 2017

(30) Foreign Application Priority Data
Sep. 26, 2014    (EP) ..................................... 14186593

(51) Int. Cl.
*A61B 6/00*    (2006.01)
*G01T 1/24*    (2006.01)
*A61B 6/03*    (2006.01)

(52) U.S. Cl.
CPC .............. *G01T 1/244* (2013.01); *A61B 6/032* (2013.01); *A61B 6/4488* (2013.01); *G01T 1/247* (2013.01)

(58) Field of Classification Search
CPC ... A61B 6/4283; A61B 6/4405; A61B 6/4233; G03B 42/04; G03B 42/02
See application file for complete search history.

(56) References Cited

U.S. PATENT DOCUMENTS

| 8,093,535 B2 | 1/2012 | Heismann |
| 8,304,739 B2 | 11/2012 | Van Veen |
| 8,575,558 B2 | 11/2013 | Tkaczyk |
| 8,659,148 B2 | 2/2014 | Tkaczyk |
| 2003/0016779 A1* | 1/2003 | Pohan .................... A61B 6/035 378/19 |

(Continued)

FOREIGN PATENT DOCUMENTS

| DE | 10138913 | 3/2003 |
| WO | 2014/072939 | 5/2014 |

*Primary Examiner* — Hoon Song

(57) ABSTRACT

The invention relates to a radiation detector (100') and a method for detecting radiation, particularly for detecting X-rays (X) in a CT imaging apparatus (1000'). According to a preferred embodiment, the radiation detector (100') comprises a conversion element (110) for converting incident radiation (X) into electrical signals which are read out and processed by a readout circuit (120). A heating device comprising the heat source (135') of a Peltier element is provided with which the conversion element (110) can controllably be heated in order to reduce negative effects, e.g. of polarization, on image accuracy, wherein the heat sink (137') of the Peltier element is oriented towards the readout circuit.

12 Claims, 3 Drawing Sheets

(56) References Cited

U.S. PATENT DOCUMENTS

| | | | |
|---|---|---|---|
| 2003/0043959 A1* | 3/2003 | Wischmann | G01T 1/2018 |
| | | | 378/19 |
| 2007/0029496 A1 | 2/2007 | Bouhnik | |
| 2009/0101828 A1* | 4/2009 | Nakata | A61B 6/4233 |
| | | | 250/370.15 |
| 2009/0152472 A1 | 6/2009 | Kim | |
| 2010/0327173 A1 | 12/2010 | Woychik | |
| 2011/0049381 A1 | 3/2011 | Luhta | |
| 2013/0248729 A1 | 9/2013 | Hannemann | |
| 2015/0139390 A1* | 5/2015 | Bellazzini | G01N 23/04 |
| | | | 378/62 |
| 2016/0029985 A1* | 2/2016 | Kato | A61B 6/035 |
| | | | 378/19 |

* cited by examiner

RADIATION DETECTOR WITH HEATING DEVICE

CROSS REFERENCE TO RELATED APPLICATIONS

This application is the U.S. National Phase application under 35 U.S.C. §371 of International Application No. PCT/EP2015/070992, filed Sep. 15, 2015, published as WO 2016/046014 on Mar. 31, 2016, which claims the benefit of European Patent Application Number 14186593.1 filed Sep. 26, 2014. These applications are hereby incorporated by reference herein.

FIELD OF THE INVENTION

The invention relates to a radiation detector comprising a heating device and a conversion element for the conversion of incident radiation into electrical signals. Moreover, it relates to methods for operating a radiation detector and to an imaging apparatus comprising the mentioned radiation detector.

BACKGROUND OF THE INVENTION

The US 2013/248729 A1 discloses a radiation detector that is used for the detection of X-radiation in a Computed Tomography (CT) apparatus and that comprises a direct conversion material in which incident X-rays are converted into electrical signals. The electrical signals are read out and processed by an Application Specific Integrated Circuit (ASIC) disposed adjacent to the conversion element. In order to stabilize the temperature of the conversion element and the ASIC, heating elements are integrated into the ASIC and operated in such a manner that the total electrical power of the detector is kept constant.

Furthermore, the US 2007/029496 A1, US 2003/043959 A1, US 2011/049381 A1, and US 2009/152472 A1 disclose radiation detectors with means for heating a converter element. The DE 101 38913 A1 discloses a radiation detector in which a Peltier element is used for heating or cooling a sensor array and associated control electronics.

SUMMARY OF THE INVENTION

It would be advantageous to provide means that allow for the operation of a radiation detector with increased accuracy and stability.

This object is addressed by a radiation detector according to claim 1, a method according to claim 2, and an imaging apparatus according to claim 3. Preferred embodiments are disclosed in the dependent claims.

According to a first aspect, the invention relates to a radiation detector for detecting incident radiation, particularly radiation such as X- or gamma radiation. The radiation detector comprises the following components:

A conversion element for converting incident radiation into electrical signals.
A readout circuit for processing said electrical signals.
A heating device for heating said conversion element, wherein the heating device is (spatially) separated from the readout circuit.

Moreover, the heating device comprises a Peltier element, wherein the heat source of said Peltier element is oriented towards the conversion element and its heat sink is oriented towards the readout circuit.

The conversion element will typically comprise a block or body of some appropriate (homogeneous or inhomogeneous) bulk material in which incident rays are converted into electrical signals. Suited materials for the conversion of X-rays into charge signals are for example CdTe, CdZnTe (CZT), CdTeSe, CdZnTeSe, CdMnTe, InP, $TlBr_2$ or $HgI_2$ or other "direct conversion materials". Moreover, the conversion element will usually comprise electrodes via which an electrical field can be generated in the bulk material and via which charge signals can be read out. By an appropriate spatial arrangement of said electrodes, a pixelated structure can be created that allows for a spatially resolved detection of incident radiation.

The readout circuit is intended and designed for reading out the electrical signals generated by radiation in the conversion element and for appropriately (pre-)processing them, for example by amplifying, filtering, integrating, classifying and/or counting electrical signals such as charge pulses. The readout circuit may particularly be realized by an ASIC. More information about a typical design of a conversion element and an associated readout circuit may for example be found in the WO 2014/072939 A1.

The heating device shall be a component that is spatially separated from the readout circuit and that is designed and arranged to generate heat which is (at least partially) taken up by the conversion element. Preferably most or all of the heat generated by the heating device is taken up by the conversion element while no or only a minor part reaches the readout circuit (without first passing through the conversion element). The heating device will preferably be an element or component the only function and purpose of which is to generate/dissipate heat. Furthermore, it may in particular be designed such that it can selectively and controllably generate heat, for example under the regime of some external controller.

According to the invention, the heating device comprises a Peltier element. With a Peltier element, a heat source can be established at one location and a heat sink can be established at another location under electrical control. Thus both heating and cooling can be realized with one controllable device. Moreover, the heat source of the Peltier element is oriented towards the conversion element and the heat sink of the Peltier element is oriented towards the readout circuit. Cooling of the readout circuit can thus be combined with heating of the conversion element.

According to a second aspect, the invention relates to a method for operating a radiation detector of the kind described above. The method comprises (at least) the following steps, which may be executed in the listed sequence, in reverse order, or most preferably simultaneously:

Converting incident radiation into electrical signals with the help of a conversion element.
Actively heating said conversion element to a temperature of at least 50° C.

In preferred embodiments of this method, the temperature to which the conversion element is heated is higher than about 55° C., higher than about 60° C., higher than about 65° C., higher than about 70° C., or higher than about 80° C.

According to a third aspect, the invention relates to a further method for operating a radiation detector of the kind described above. The method comprises (at least) the following steps, which may be executed in the listed sequence, in any other order, or most preferably simultaneously:

Converting incident radiation into electrical signals with the help of a conversion element.
Processing said electrical signals in a readout circuit.

Actively heating the conversion element, substantially without simultaneously heating the readout circuit.

In this context, "substantially" means that preferably more than about 50%, more than about 70%, or most preferably more than about 90% of the actively generated heat energy reach the conversion element (and not the readout circuit).

Heating of the conversion element substantially without heating of the readout circuit can for example be achieved by an appropriate arrangement of a heating device (e.g. closer to the conversion element than to the readout circuit) and/or by inserting appropriate thermal barriers (insulating layers).

Moreover, the readout circuit is preferably simultaneously cooled by the heat sink of the Peltier element of the radiation detector.

The method according to the third aspect can particularly be combined with the method of the second aspect, i.e. the conversion element can be heated to a temperature of at least about 50° C.

The radiation detector and the methods according to the first, second and third aspects of the invention are based on the general approach to actively heat a conversion element without inevitably also heating an associated readout circuit. This approach is based on the insight that an operation of a conversion element at higher temperatures can have positive effects on signal accuracy and stability, for example via a reduction of polarization (i.e. the buildup of space charge that weakens an externally applied electrical field). Hence an optimal temperature range for operating the conversion element can be found in which the positive effects of heat (e.g. of a reduced polarization) and negative effects (e.g. dark current) are balanced. Typically, this temperature range is higher than the temperature range at which the readout circuits operate with highest accuracy. The conversion element and the readout circuit are therefore preferably operated at different temperatures.

This can very efficiently be achieved with the help of the Peltier element of the radiation detector that allows for simultaneously heating the conversion element and cooling of the readout circuit.

Preferred ranges for the operation temperature of the conversion element are for example between about 50° C. and about 60° C., between about 60° C. and about 70° C., or between about 70° C. and about 80° C.

The invention further relates to an imaging apparatus for generating images of an object, said imaging apparatus comprising the following components:

A radiation source for generating radiation.

A radiation detector of the kind described above for detecting said radiation, particularly after interaction of the radiation with some object, for example after transmission through the body of a patient.

The imaging apparatus may particularly be an X-ray device, for instance a fluoroscopic device, a Computed Tomography (CT) imaging system, for instance a photon-counting Spectral CT imaging system, or a Coherent Scatter Computed Tomography (CSCT) imaging system.

In the following, various preferred embodiments of the invention will be disclosed that can be realized in connection with the radiation detector, the imaging apparatus and/or a method of the kind described above (even if they are described in detail only for one of these).

The operating temperature of the conversion element (which, according to the invention, can actively be affected) may preferably be higher than the temperature of the readout circuit. The temperature to which the conversion element is heated may particularly be higher by more than about 10° C., more than about 20° C., or more than about 30° C. than that of the readout circuit.

There are various possibilities how active heating of the conversion element can be achieved and how the heating device of the radiation detector can be realized in addition to the usage of the heat source of a Peltier element. Heat can for example be transported to a target location by forced convection of a medium such as hot air. In a preferred embodiment, heating is achieved with a heating device that comprises resistive electrical lines or structures (patterns). An electrical current flowing through these lines/structures will then generate heat due to the Ohmic resistance which is dissipated into the surroundings. An advantage of a heating device consisting of or comprising resistive lines is that it can cost efficiently be realized and that the generation of heat can readily be controlled by adjusting the electrical current.

Two basic design components of the radiation detector are the conversion element and the readout circuit. According to a preferred embodiment, the radiation detector further comprises an "additional layer" that is disposed adjacent to a surface of the conversion element. In this context, the term "adjacent" means that the additional layer is located close to said surface, for example not farther away than a distance corresponding to the thickness of the conversion element. Preferably, there is no other solid component between said surface of the conversion element and the additional layer, and the additional layer may even optionally contact said surface. As will be explained below with reference to preferred embodiments of the invention, the additional layer can favorably be exploited to improve the operational behavior of the radiation detector, particularly with respect to a temperature control in the conversion element.

In an optional further development of the aforementioned embodiment, the additional layer comprises the heating device. The heating device may for example have the shape and configuration of a layer and be identical to the additional layer or at least to a sub-layer thereof. For other configurations, for example if the heating device is realized by or includes resistive electrical lines, the heating device may be integrated into the additional layer and/or disposed on a surface of the additional layer. In the latter case, it is preferably disposed on that surface of the additional layer that faces the adjacent surface of the conversion element. Heat generated by the heating device can then immediately pass over to the conversion element.

The conversion element usually has a first surface that is directed towards the readout circuit and a second surface facing in opposite direction. The abovementioned additional layer may optionally be disposed adjacent to said first surface, i.e. it may be interposed between the conversion element and the readout circuit, or it may be disposed adjacent to said second surface. Moreover, the radiation detector may comprise two additional layers, one of them being located adjacent to the first and the other being located adjacent to the second surface of the conversion element. An additional layer adjacent to the first surface (i.e. interposed between the conversion element and the readout circuit) has the advantage to thermally separate the conversion element from the readout circuit such that a temperature difference between the two can more easily be maintained. An additional layer adjacent to the second surface has the advantage to isolate the conversion element from the environment, thus reducing heat losses and supporting the maintenance of a high temperature of the conversion element. Moreover, heat generated in such an additional layer could only reach the readout circuit (which is not desired) after first passing through the conversion element (which is desired). Hence this heat is optimally directed towards its actual target.

In another embodiment of a radiation detector with an additional layer, that layer may comprise electrical components. Most preferably, it may comprise simple electrical lines for electrically connecting components to each other, particularly vias (which by definition cross the thickness of the layer) by which electrodes (e.g. anodes) on the surface of the conversion element are connected to terminals of the associated readout circuit. Additionally or alternatively, the additional layer may comprise vias or electrical lines for supplying the heating device with electrical power.

The additional layer may optionally consist of a single, homogeneous material, or it may have an inhomogeneous structure, consisting for example of a stack of several sublayers. Preferred materials for the single layer and/or for any one of the stacked sublayers are for example silicon, glass, sapphire ($Al_2O_3$), quartz ($SiO_2$), AlN, or polymers like FR4, LTCC (Low Temperature Cofired Ceramics), polyamide or polyimide. Appropriate materials can be chosen according to their electrical and/or thermal properties. Thermally insulating layers may for example be interposed between the heating device and the readout circuits, or thermally conductive layers may be interposed between the heating device and the conversion element. Moreover, an electrical heating device, consisting for example of resistive electrical lines, may preferably be embedded between electrically insulating sublayers.

According to another embodiment of the invention, a thermally conductive material, called "underfill" in the following, may be disposed between the heating device and the conversion element. The underfill can thermally bridge gaps that may exist between the conversion element and the heating device, for example caused by electrical terminals. The underfill may for example comprise polymers, resins and/or epoxy based underfill (commercially available for example as Hysol®, Ecobond®, Epotek 301, or Delo 6823).

Additionally or alternatively, a thermally insulating material may optionally be disposed between the conversion element and/or the heating device on the one hand side and the readout circuit on the other hand side in order to protect the latter from heat. The insulating layer may particularly be identical to the above mentioned additional layer or to a sublayer thereof. Moreover, it should be noted that, in the context of the present invention, a material is considered as being "thermally conductive" if it has a heat conductivity higher than about 50 $Wm^{-1}K^{-1}$, preferably higher than about 100 $Wm^{-1}K^{-1}$. Similarly, a material is considered as being "thermally insulating" if it has a heat conductivity lower than about 50 $Wm^{-1}K^{-1}$, preferably lower than about 30 $Wm^{-1}K^{-1}$.

The radiation detector may optionally further comprise a temperature sensor for determining the temperature of the conversion element. The temperature sensor may for example be a thermocouple disposed in contact to the conversion element such that its temperature can directly be measured, or disposed remote from the conversion element and providing information from which the temperature of the conversion element can be estimated. Additionally or alternatively, the temperature sensor may comprise a resistive structure built analogously to a heating device made from resistive lines/structures. Knowledge of the temperature of the conversion element can be used in various ways, for example to prevent an overheating of the conversion element.

According to another embodiment of the invention, the radiation detector comprises a control loop for controlling the operation of the heating device. This embodiment may particularly be combined with the aforementioned one, using the temperature sensor for the creation of a closed control loop by which the temperature of the conversion element can be kept in some target range.

The radiation detector may further optionally comprise a cooling device for selectively cooling the conversion element and/or the readout circuit. The cooling device may for example use circulated air for removing excessive heat. Cooling of the readout circuit is particularly important as high temperatures induce thermal noise.

The heat sink of the Peltier element may particularly function as such a cooling device.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

X-ray detectors as they are for example used in CT imaging apparatuses may be built with direct conversion ("DiCo") materials that directly convert incident X-ray photons into electrical signals (typically a cloud of electrical charges). Direct conversion materials (e.g. CdZnTe) show reduced tendency to being polarized (i.e. building up a space charge which weakens the externally applied electric field) at increasing bulk temperatures. Due to the effect that temperature has on releasing trapped charges, the onset of polarization artefacts can thus be improved, disappearing completely or appearing only at higher photon fluxes. The mitigation or elimination of polarization effects at least partially outweighs the negative impact of operating at high temperatures (e.g. increased dark current).

A direct converting detector is usually assembled/placed on a readout ASIC which dissipates heat, thus increasing the temperature of the conversion bulk material. However, the ASIC cannot serve as a temperature regulator as the dissipation generated solely depends on the operating point designed to yield adequate electrical performance. A limited control of the temperature can only be achieved by controlling the cooling (heat dissipation) of the ASIC itself, which has only an indirect influence on the conversion bulk material.

It is therefore proposed here to (largely) decouple the heating of the conversion material and the cooling of the ASIC.

Moreover, interposers (i.e. electrical interface layers routing between one connection to another) are often required to interface direct converting sensors to readout ASICs, particularly for achieving 4-side tileable concepts. The interposer materials (and vias) determine the heat transport through this layer. It is therefore further proposed to equip the interposer material (or, more generally, an additional layer) with a heating device (e.g. comprising resistive wires) on one side (preferably the side facing the DiCo). The purpose of this heating device is to produce regulated heat and to monitor the temperature.

Figure 1:
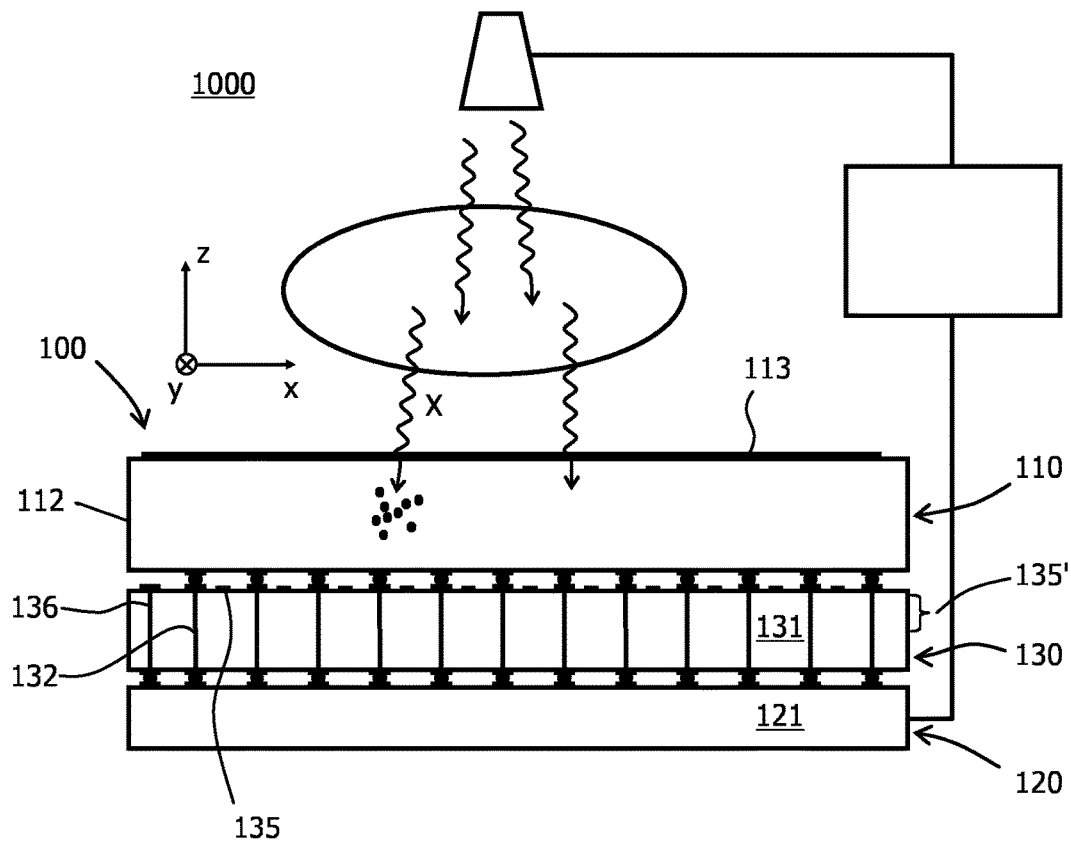
FIG. 1 schematically shows a cross section of an imaging apparatus with a radiation detector in which an additional layer with a heating device is disposed between the conversion element and the readout circuit.

FIG. 1 schematically shows a cross section of an imaging apparatus 1000 according to a first preferred embodiment of the above general principals. The imaging apparatus 1000 may for example be a Computed Tomography (CT) device as it is generally known in the art. It comprises a radiation source such as an X-ray tube, S, for emitting X-rays X that are transmitted through an object to image, for example through the body P of a patient. After transmission through the object, the X-rays reach a radiation detector 100 where they are detected and converted into signals representing a spatially resolved projection image of the object. In a computer C connected to the radiation detector 100 and the radiation source S, projection images and particularly 3D images of the object can then be reconstructed according to known principles of Computed Tomography.

The component of particular interest here is the radiation detector 100. This detector 100 comprises a stack of the following components, listed from bottom to top in z-direction (which is antiparallel to the main direction of incidence of X-rays):

a) A readout circuit 120 comprising an ASIC 121 in which electrical signals of the conversion element 110 (cf. below) are processed, for example amplified, filtered, pulse-counted and/or energy discriminated. The bottom side of the readout circuit 120 is available for I/O (e.g. through TSVs) and cooling (not shown).

b) A layer 130 that is in the following called "additional layer" or "interposer" and that substantially consists of an electrically insulating substrate 131, e.g. a glass plate, with a plurality of electrically conductive lines or "vias" 132, 136 leading from its bottom side to its top side. At the bottom side, first vias 132 are (one-to-one) connected to terminals on the top side of the readout circuit 120. Moreover, (two) second vias 136 are provided for supplying power from the readout circuit 120 to a heating device 135 on the top side of the interposer 130. The vias 132, 136 may for example consist of copper.

In the shown embodiment, the additional layer 130 preferably is or comprises a Peltier element, wherein the heat source 135' of said Peltier element is oriented towards the conversion element 110 and its heat sink is oriented towards the readout circuit 120.

Figure 2:
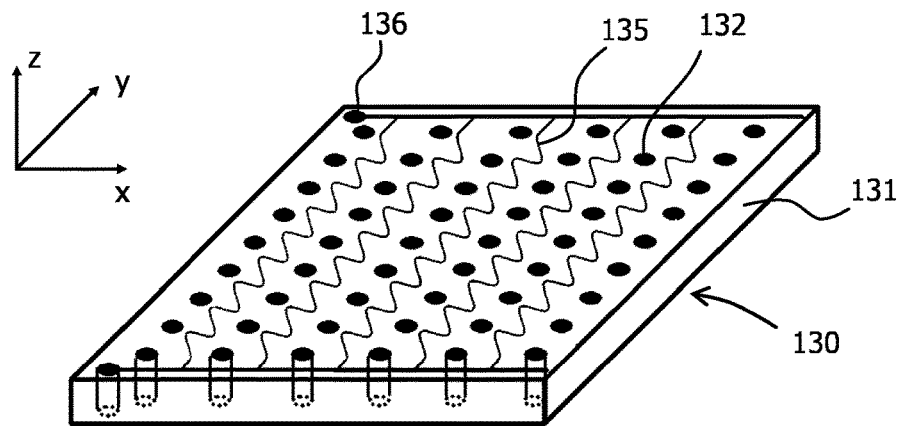
FIG. 2 shows a perspective view of an additional layer with a heating device on top.

FIG. 2 shows a perspective view onto the interposer 130 alone from which the vias or "pixel interconnects" 132 and the supply contacts 136 for the heating device (resistive wiring) can better be seen. The resistive wiring 135 can be deposited (e.g. by printing, lithography, or plating) on the top surface of the interposer 130. The supply contacts 136 can be distributed also through the interposer to the ASIC. In general, the supply can be provided in different ways: A) generated/controlled by the ASIC (as shown in FIG. 1), B) externally though the assembly I/O, or C) externally but distributed by the ASIC.

c) Returning to FIG. 1, the detector 100 further comprises a conversion element 110 comprising a block 111 of a suitable converter material such as CZT (CdZnTe) in which incident X-rays are converted into electrical signals, particularly charge clouds. The charge clouds move under the influence of an electrical field that is generated between a cathode 113 on the top side of the conversion element 110 and an array of anodes 112 on the bottom side of the conversion element. The anodes 112 are connected (one-to-one) to the first vias 132 of the interconnect 130 and hence to the associated pixel terminals of the readout circuit 120. Thus charge signals generated by incident X-rays can be detected by the readout circuit 120 as generally known the state of the art, for example by energy-discriminating pulse counting.

The interposer 130 used to interface the conversion element 110 and the readout ASIC 120 can be made of a number of different materials, preferably materials that have a low heat conductivity and/or that match the thermal expansion coefficients of other components of the radiation detector. Possible materials for its substrate 131 comprise for example Si, glass (with a typical thermal expansion coefficient of about $3.3-8.5 \cdot 10^{-6}$ $mK^{-1}$), sapphire ($Al_2O_3$), quartz ($SiO_2$), AlN, and polymers like FR4, LTCC, polyamide, or polyimide. In all cases, it is possible to deposit a resistive wiring grid (e.g. by thin film processing) that serves as a heating device and generates heat when an electrical current flows through it. This is particularly suitable for silicon or glass substrates 131, not unlike the rear (and sometimes also front) windshield defrosting in automobiles ("defoggers") or devices used in MEMS technology. The wiring grid 135 (in the embodiment of FIG. 2 a set of parallel resistors) may be placed on the substrate 131 or within a stack of layers, like AlN, $SiO_2$, or $Al_2O_3$. During operation of the radiation detector 100, the wiring grid 135 can produce heat and increase the temperature of the DiCo material 111. To maximize the heat transfer to the DiCo material 111, after assembly an underfill material (not shown) can be used that exhibits good thermal conductivity.

An additional sub-layer (not shown) with a good heat conductivity (e.g. AlN) can optionally be used to electrically isolate the electrical wires 135. By implementing a second heat blocking layer (e.g. $Al_2O_3$, if matching of thermal expansion coefficients is needed, or $SiO_2$ with lower heat conductivity), the heat flow via, for example, copper vias can be reduced. This will create a better heat separation.

The current or voltage applied to the resistive wiring 135 can be controlled to regulate the surface temperature to which the DiCo substrate 111 is attached.

Moreover, the current or voltage applied to an optional Peltier element included in the interposer 130 can in addition be controlled to heat the conversion element 110 and to simultaneously cool the ASIC 120.

The ASIC 120 may still be cooled down independently at its bottom side (not shown).

For the purpose of regulating the temperature of the resistive grid 135, a temperature-measuring device (e.g. a thermocouple, not shown) can optionally be integrated within the interposer substrate 131 to the effect of providing a feedback mechanism. Additionally or alternatively, a wiring (not shown) similar to that of the heating element 135 can optionally be used to measure the temperature, wherein the measurement signal can be used as feedback for the heating or cooling. The temperature information can be also made available in a similar manner as the grid supply lines.

The interposer 130 provides the pixel interconnection from the conversion element 110 to the ASIC 120. In the example shown in FIG. 1, a 1:1 connection is assumed. Redistributing the pixel connection within the interposer substrate is however possible, too.

In another embodiment of the invention, it is proposed to use an interconnect substrate on the cathode side of the DiCo material. Polarization effects typically originate close to the cathode side of the DiCo material. This indicates that it may be beneficial to have a heat source on the cathode side. In such a configuration a better decoupling between the conversion material heating and the ASIC cooling can be achieved.

Figure 3:
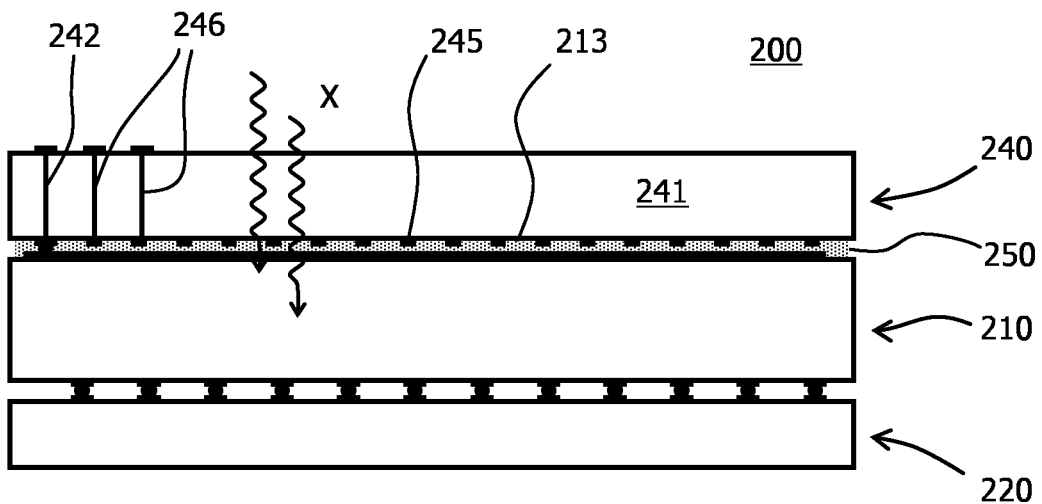
FIG. 3 schematically shows a side view of a radiation detector in which an additional layer with a heating device is disposed on the conversion element.

FIG. 3 schematically shows a side view of a radiation detector 200 in which the aforementioned concept is realized. An additional layer 240 or "interposer" with a resistive wiring 245 on its bottom side is disposed on top of a conversion element 210, e.g. a CTZ block. Besides vias 246 for the supply of electrical power to the resistive wiring 245 and a high-voltage contact 242, no further vias or lines are needed.

In order to avoid absorption of X-ray photons in the additional layer 240 above the cathode 213, this layer has to be sufficiently thin and/or should comprise a material with low atomic weight elements such as Al. The wires will anyway have a small diameter in order to enable heating. Optionally one can have multiple heaters per CZT tile to optimize the heat stability. Heating devices may for example cover only part of the DiCo material, making it possible to only locally heat the material. Thus polarization on parts of the DiCo material can be decreased without increasing the dark current on the other parts by having them at lower temperatures.

A readout circuit 220 is directly bonded (e.g. flip-chip bonded) to the anodes on the bottom side of the conversion element 210. Besides this, the readout circuit 220 and the conversion element 210 may substantially be built identical to those of the first radiation detector 100 described above.

A gap that may remain between the resistive wiring 245 on the bottom side of the additional layer 240 and the cathode 213 on the top side of the conversion element 210 may optionally be filled with a thermally highly conductive underfill material 250.

In the embodiment of the radiation detector 200, the electrical heating device 245 is placed on the interposer interface facing the conversion material 210. The electrical heating device can also be placed on the top side of the interposer (not shown), particularly if the interposer is made of a good heat conductive material, for example AlN. Optionally a heat blocking layer could be applied on top of such a heating device to decrease the heat losses to the air.

Figure 4:
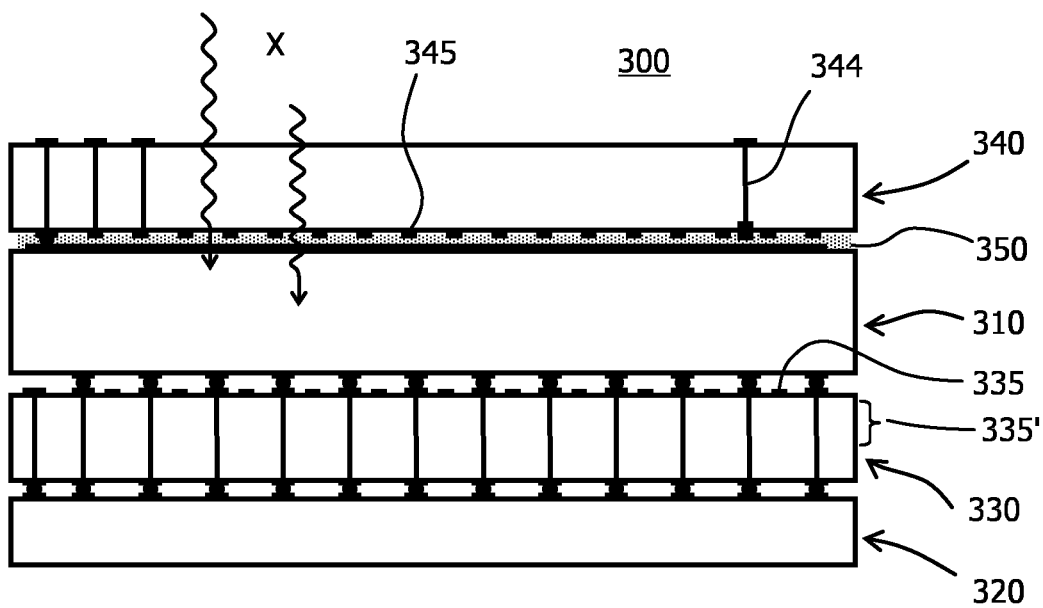
FIG. 4 schematically shows a side view of a radiation detector in which a conversion element is sandwiched between two additional layers with heating devices.

FIG. 4 shows an embodiment of a radiation detector 300 which is essentially the combination of the first and second embodiments shown in FIGS. 1 and 3. This means that a first additional layer 330 is disposed between a readout circuit 320 and a conversion element 310, having a heating device 335 on its top side that faces the conversion element. Moreover, a second additional layer 340 is disposed on top of the conversion element 310 with a heating device 345 on its bottom side facing the cathode of the conversion element. Again, a thermally conductive underfill 350 may fill the gap between the cathode and the heating device. Besides this, the design of the conversion element 310, the first additional layer 330, and the readout circuit 320 may be analogous to that of the corresponding elements 110, 130, and 120 in FIG. 1, and the design of the conversion element 310 and the second additional layer 340 may be analogous to that of the corresponding elements 210 and 240 in FIG. 3.

The additional layer 330 may preferably comprise a Peltier element, wherein the heat source 335' of said Peltier element is oriented towards the conversion element 310 and its heat sink is oriented towards the readout circuit 320.

By arranging heating devices and additional layers 330, 340 on both sides of the conversion element 310, temperature gradients within the bulk can be minimized.

FIG. 4 further illustrates the presence of a thermocouple 344, here realized in the second additional layer 340, with which a control loop for the temperature in the conversion element 310 can be established.

A Peltier element can be used to act as interposer between a conversion element and a readout circuit (ASIC). With other words, the additional layers 130, 240, 330 and 340 can be Peltier elements, wherein a separate resistive wiring could optionally be omitted. The Peltier element would typically require incorporation of pixel interconnection vias (such as vias 132 in FIG. 1). The hot side of the Peltier element could preferably be arranged to be in contact with the anode side of the conversion element, whereas the cooling side of the Peltier element would be in contact with the readout circuit.

Figure 5:
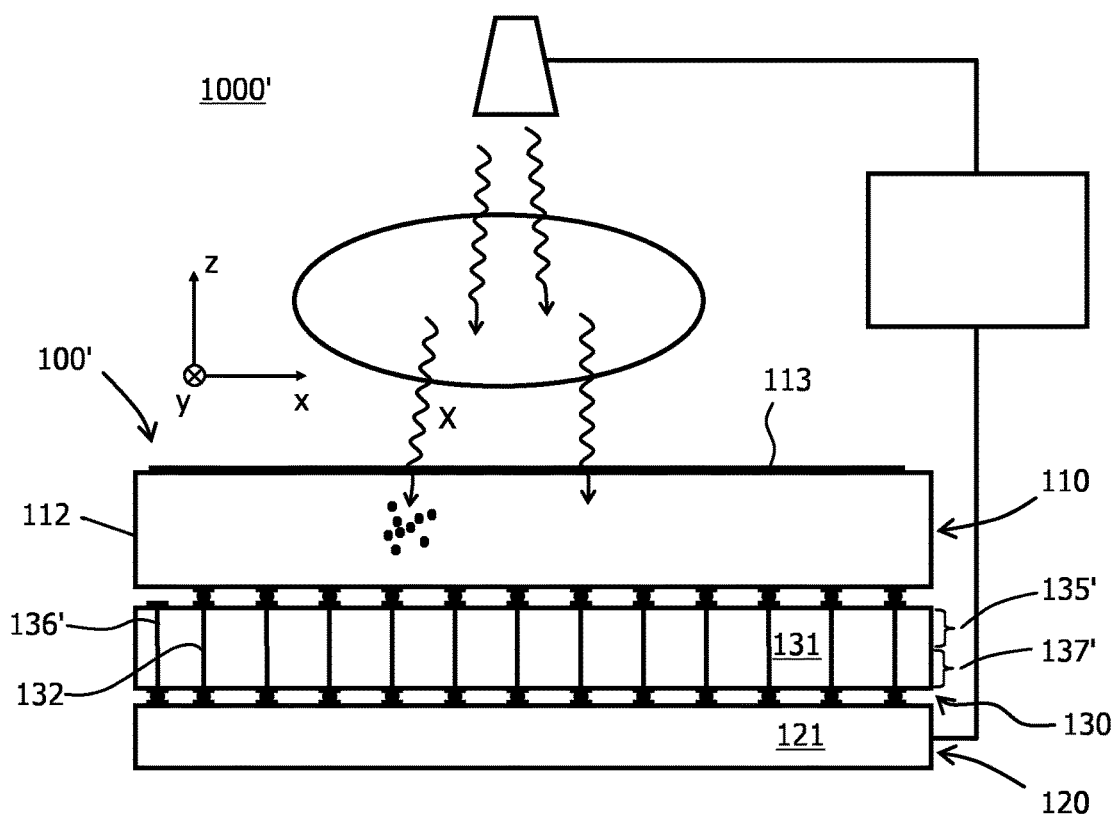
FIG. 5 schematically shows a cross section of an imaging apparatus with a radiation detector in which a Peltier element is disposed as an additional layer between the conversion element and the readout circuit.

FIG. 5 illustrates the implementation of the aforementioned aspects for an imaging apparatus 1000' that is a modification of the apparatus of FIG. 1 and that comprises a modified radiation detector 100'. Components that are identical to those of FIG. 1 have identical reference signs and will not be explained again.

The interposer or additional layer 130 of the radiation detector 100' comprises (or is) a Peltier element, the heat source 135' of which is oriented towards the conversion element 110 and acts as a heating device. The heat sink 137' of this Peltier element is oriented towards the readout electronics 120. Electrically conductive lines or "vias" 136' may be provided for supplying power from the readout circuit 120 to the Peltier element. Contrary to the embodiment of FIG. 1, the heating device comprises no additional resistive wiring.

Figure 6:
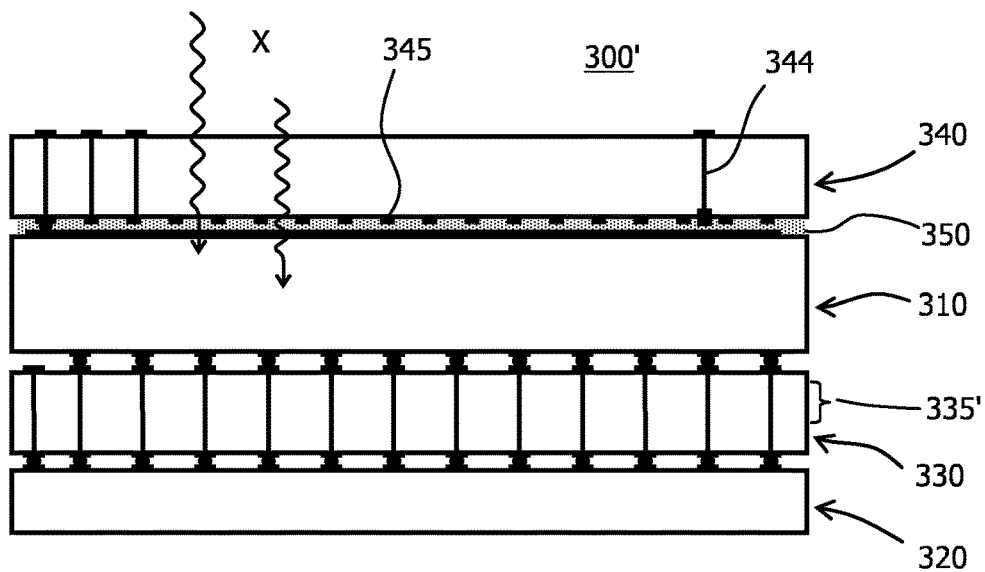
FIG. 6 schematically shows a side view of a radiation detector in which a conversion element is sandwiched between two additional layers.

FIG. 6 shows a radiation detector 300' which is essentially the combination of the embodiments shown in FIGS. 5 and 3. This means that a first additional layer 330 is disposed between a readout circuit 320 and a conversion element 310, having the heat sink 335' of a Peltier element as a heating device at its top side that faces the conversion element. Moreover, a second additional layer 340 is disposed on top of the conversion element 310 with a heating device 345 on its bottom side facing the cathode of the conversion element. Other components of the radiation detector 300' are identical to those of FIGS. 3, 4 and 5 and have identical reference signs.

In summary, it has been noticed that direct conversion materials (e.g. CdZnTe) show a reduced tendency to being polarized at increasing bulk temperatures. Due to the effect that temperature has on releasing charge trapping, the onset of polarization artefacts can be improved, disappearing completely or appearing only at higher photon fluxes. The elimination of polarization effects outweighs the negative effects of operating at high temperatures (e.g. dark current). Based on this background an approach has been proposed to (largely) decouple the heating of the conversion material and the cooling of the ASIC. In some embodiments of a radiation detector, interposers are required to interface direct converting sensors to readout ASICs, particularly for achieving 4-side tileable concepts. It is suggested to equip the interposer material with a heating device (e.g. resistive wires) to produce regulated heat.

The radiation detectors according to the invention may for example be applied for CT detectors, particularly Spectral CT detectors based on direct conversion sensors.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A radiation detector comprising:
    a conversion element for converting incident radiation into electrical signals;
    a readout circuit for processing said electrical signals;
    a heating device, separated from the readout circuit, for heating the conversion element, wherein the heating device comprises a Peltier element and wherein the heat source of said Peltier element is oriented towards the conversion element and its heat sink is oriented towards the readout circuit.

2. A method for operating a radiation detector according to claim 1, said method comprising the following steps:
    converting incident radiation into electrical signals with the help of a conversion element;
    processing said electrical signals in a readout circuit;
    actively heating the conversion element without simultaneously heating the readout circuit.

3. An imaging apparatus for generating images of an object, particularly a CT imaging apparatus, comprising:
    a radiation source for generating radiation;
    a radiation detector according to claim 1 for detecting said radiation.

4. The radiation detector according to claim 1, characterized in that the heating device comprises resistive lines or structures.

5. The radiation detector according to claim 1, characterized in that it comprises an additional layer disposed adjacent to a surface of the conversion element.

6. The radiation detector according to claim 5, characterized in that the additional layer comprises the heating device.

7. The radiation detector according to claim 5, characterized in that the additional layer is disposed adjacent to the surface of the conversion element that is directed towards the readout circuit or adjacent to the surface opposite thereto.

8. The radiation detector according to claim 5, characterized in that the additional layer comprises vias for electrically connecting the conversion element to the readout circuit and/or the heating device to an electrical power supply.

9. The radiation detector according to claim 1, characterized in that a thermally conductive material is disposed between the heating device and the conversion element and/or that a thermally insulating material is disposed between the conversion element and/or the heating device and the readout circuit.

10. The radiation detector according to claim 1, characterized in that it comprises a temperature sensor for determining the temperature of the conversion element.

11. The radiation detector according to claim 1, characterized in that it comprises a control loop for controlling the operation of the heating device.

12. The radiation detector according to claim 1, characterized in that it comprises a cooling device for selectively cooling the conversion element and/or the readout circuit.

* * * * *